United States Patent
Magee et al.

[11] 3,990,778
[5] Nov. 9, 1976

[54] OPTICAL VIEWING SYSTEM FOR HIGH PRESSURE ENVIRONMENTS

[75] Inventors: Robert J. Magee, Concord; Bernard J. Murphy, Westford, both of Mass.

[73] Assignee: Charles Stark Draper Laboratory, Inc., Cambridge, Mass.

[22] Filed: Sept. 4, 1975

[21] Appl. No.: 610,428

[52] U.S. Cl. ............................. 350/96 BC; 350/34
[51] Int. Cl.² ............................................. G02B 5/17
[58] Field of Search ................. 350/96 R, 96 BC, 34

[56] References Cited
UNITED STATES PATENTS
3,136,208   6/1964   Magson ..................... 350/96 BC

*Primary Examiner*—John K. Corbin
*Assistant Examiner*—Rolf Hille
*Attorney, Agent, or Firm*—Weingarten, Maxham & Schurgin

[57] ABSTRACT

A fiber optic system for permitting viewing of any of a plurality of selectable remote scenes in hostile environments by direct image transmission to the observer outside of the environment of the scenes. An optical image of each scene is transmitted by separate fiber optic bundles to an optical selector system which redirects the transmitted image through a single bundle where the image is presented in a form for viewing by the observer. The system is particularly useful in troublesome environments such as are encountered in the high pressures outside vessels or noise radiation sources where conventional television viewing systems can be used only with special insulation or containment.

12 Claims, 5 Drawing Figures

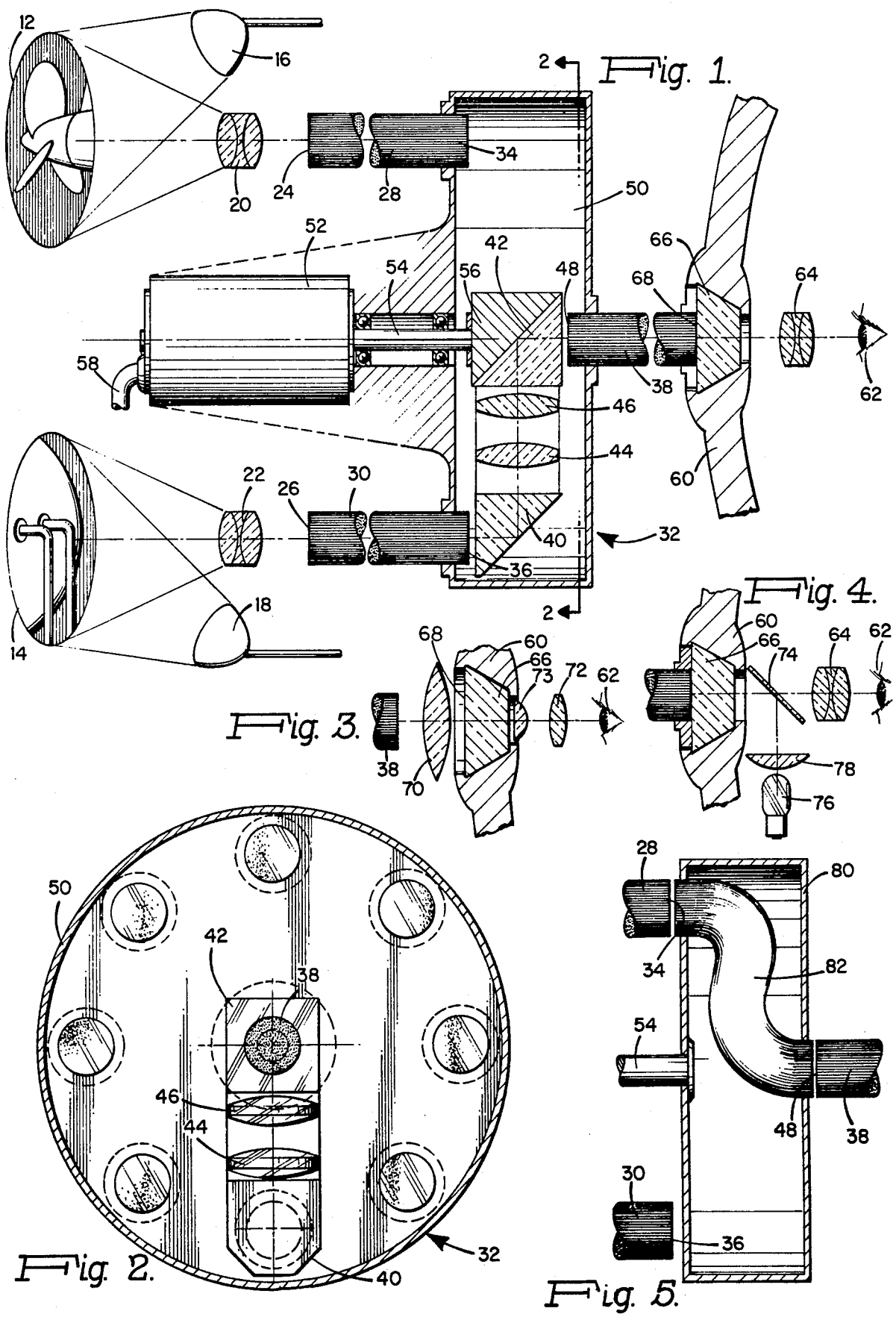

OPTICAL VIEWING SYSTEM FOR HIGH PRESSURE ENVIRONMENTS

FIELD OF THE INVENTION

The present invention relates to remote viewing systems and in particular to a fiber optic system for direct viewing of scenes in a hostile environment remote from the observer.

BACKGROUND OF THE INVENTION

The closed circuit television (TV) system is a well known technique for the viewing of remote objects in hostile surroundings such as high pressure environments such as the exterior of a deep diving vessel or in certain high pressure processes. The closed circuit TV system, however, requires substantial power which may be impractical in remote environments of deep diving vessels and in addition requires an expensive high pressure containment for the television transmitter, as well as associated cables and connectors through pressure vessels. In particular, wide bandwidth low signal level connections through pressure vessels are complicated. In addition, the weight of the television transmission and receiving equipment, as well as the volume loss in confined spaces makes such systems less than ideal. Where several scenes within the high pressure environment are to be viewed, plural television monitoring transmitters must be employed greatly increasing the disadvantages in cost and weight of the TV system. Where color is also desired in the closed circuit TV system, an additional complexity in cost, bulk, and transmission bandwidth is present.

There exist other applications for remote viewing where the hostility of the invironment places restrictions on the use of closed circuit TV systems as to greatly increase their cost and complexity. One example includes visual monitoring of objects in an environment exposed to intense radiation such as radio frequency interference that would require full shielding or more complex protection of the electronics and cables in the closed circuit system.

An alternative to the closed circuit television system would be to employ an optical periscope incorporating one or more series of lens trains which could transmit an image directly from the external environment to a viewer without intermediate electrical processing and would provide an optical quality substantially superior to that obtainable with television. Such optical periscope systems, also occupy a substantial volume, require a precise rigid alignment for accurate picture rendition and are correspondingly likely to be costly, particularly where a large number of widely separated scenes are to be viewed.

BRIEF SUMMARY OF THE INVENTION

In accordance with the teaching of the present invention, a direct fiber optic image transmission system is provided for direct viewing of a selected one of a plurality of remote scenes with hostile surroundings such as in a high pressure or high radiation environment. An image of each scene is formed onto one end of a corresponding one of a plurality of fiber optic bundles exposed to the hostile environment. Each bundle leads to an optical selector switch positioned to transmit the optical image in the selected fiber optical bundle onto a central optical bundle which applies an image for transmission through a window to a position removed from the environment. The image of the selected remote scene can then be viewed through the window with an eyepiece lens.

The selector system is preferably rotated by an electromechanical system operating within the hostile environment in response to signals from an operator to position the selector system to receive the image transmitted by a selected fiber optic bundle from the desired scene and apply it to the bundle for transmission through the window.

The selector system may comprise a single periscope system or a further fiber optic bundle. Illumination of each scene may be provided by a separate light source or by reverse transmission of viewing light through the optical system from inside the vessel.

BRIEF DESCRIPTION OF THE DRAWING

These and other features of the present invention are more fully set forth below in the detailed description of the preferred embodiment and in the accompanying drawing of which:

FIG. 1 is a schematic diagram of a fiber optic viewing system in accordance with the present invention;

FIG. 2 is an end view of a selector system for use in the fiber optic viewing system of FIG. 1;

FIG. 3 is a schematic representation of an alternative lens arrangement for transmitting an image of a remote scene formed in accordance with the present invention through the window of a vessel for viewing;

FIG. 4 is a schematic view of an alternative system for illuminating each scene through the fiber optic viewing system; and FIG. 5 is a view of an alternative image selector system.

DETAILED DESCRIPTION OF THE PREFERRED EMBODIMENT

The present invention contemplates a system for direct optical viewing of a selected one from a plurality of scenes within a hostile environment such as a high pressure fluid medium or high radiation area. The system in accordance with this invention employs fiber optic bundles which may be exposed to the hostile environment without special isolation to transmit images formed of the plurality of scenes for observation as, for example, through a window in a side of a vessel. The system of the present invention thus provides a high optical quality image of any of a plurality of remote scenes without the cost and complexity of conventional closed circuit television systems isolated from environmental effects or periscope devices with lens trains.

In accordance with the teaching of the present invention for use in a high pressure environment and as shown in FIG. 1, first and second remote scenes 12 and 14 typically represent desired objects of view in a marine deep submergence vessel such as a propeller and shaft housing shown in scene 12 or a tank with piping thereto shown in scene 14. Such scenes may either be of portions of the vehicle itself or of other underwater installations. The scenes 12 and 14 may be illuminated by lamps 16 and 18 respectively or by other illumination systems, one of which is described below.

It is to be understood that the scenes 12 and 14 are representative of typically many scenes which may be selected for viewing, eight being contemplated by the specific embodiment to be described below for the present invention.

The image from each of the scenes 12 and 14 is focused by lens systems 20 and 22 onto plane surfaces 24 and 26 which form the ends of respective fiber optic bundles 28 and 30.

The fiber optic bundles 28 and 30 are directed as necessary through the fluid medium from the corresponding scene whose image is carried by the bundle to a central location at which an optical selector system 32 is provided. The fiber optic bundles 28 and 30 may be commercially available acrylics having, for example, up to 250,000 fibers in each bundle. For this purpose, commercially available medical fiber optic bundles may also be used. Where the fluid medium is water, the interface between the fiber optic bundle and the fluid medium does not result in a significant loss of illumination carried by each fiber.

The effect of each fiber optic bundle 28 and 30 is to translate the plane of the image applied to the corresponding surfaces 24 and 26 to respective surfaces 34 and 36 at the opposite ends of the fiber optic bundles. The optical selecting system 32 operates to select and transport one of the images from the end of one of the selected fiber optic bundles to a central fiber optic bundle 38. For this purpose, the selector system 32 in a preferred embodiment consists of first and second right angle prisms 40 and 42 with a pair of relay lenses 44 and 46 interposed between the prisms. The first prism 40 reflects illumination from the translated image on the surface 36, or other surface of a different, selected fiber optic bundle. The reflected illumination is relayed by the lenses 44 and 46 by confining the expanding image as is known in the art. The image relayed by the lenses 44 and 46 is further reflected by the second prism 42 toward a surface 48 of the common fiber optic bundle 38. The relay lenses 44 and 46 are selected to provide on the surface 48 a focused image of the light pattern on the surface 36, representative of the selected scene. The prism and relay lens system illustrated in FIG. 1 is contained within a housing 50 more clearly shown in FIG. 2. While the housing 50 may protect the prism and lens system from suspended particles, the entire prism and lens system is contained within the fluid medium at ambient pressure.

Different fiber optic bundles and corresponding scenes are selected by rotation of the prisms 40 and 42 and lenses 44 and 46 together about an axis passing through the prism 42 and the fiber optic bundle 38. Rotation is preferably achieved through a stepping motor 52, or rotary solenoid, having a shaft 54 which is secured by a wedge 56 to a surface of the prism 42 in alignment with and coaxial to the axis of rotation. The motor 52 is preferably oil filled so that it can be operated at ambient pressure within a lubricating medium. Activation signals for the motor 52 are applied through a cable 58 which is typically routed through the pressure hull 60 of a vessel only partially shown. Commands from inside the vessel accomplish the rotation of the selection system in order to determine which scene is viewed by an observer 62 located within the vessel. Because the signal requirements for the motor are not wideband and low distortion, conventional pressure connectors may be used.

The observer 62 views the selected scene through an eyelens 64 and pressure window 66 in the pressure vessel 60. The fiber optic bundle 38 is directed to the window 66 with its end terminating at the outer surface 68 of the window 66. In this manner, the image from the selected one of the scenes 12, 14 . . . has been translated to the surface 68 on the exterior of the window 66 and the image available there may be focused for viewing by the eye of the observer 62 or instrumentation as desired.

The pressure window 66 is typically a clear, plastic acrylic having polished inner and outer surfaces to provide a high quality image transmission.

In an alternative embodiment of the observer view system for the present invention illustrated in FIG. 3, an objective lens 70 is located on the outside of the window 66 between the fiber optic bundle 38 and the outer surface 68. Objective lens 70 relays the image presented by fiber optic bundle 38 through window 66 to the flat surface of a field lens 73 located on the other surface of the window 66. An eyepiece lens 72 is located on the opposite side of the field lens 73 to focus the image from the field lens 73 for viewing by the observer 62.

A further alternative system is illustrated in FIG. 4. As shown there, a beam splitting element 74 is interposed between the window 66 and eye lens 64 to pass a portion, typically half, of the light through the window 66 from the selected scene to the observer 62 via the eye lens 64. A lamp 76 and condenser lens 78 are provided below the beam splitter 74 such that condensed illumination from the lamp 76 is directed by the beam splitter 74 back along the path of the fiber optic and selector system to the selected scene to provide direct illumination thereof. Such an illumination system is convenient and dispenses with additional external equipment which must operate within a high pressure environment. The illumination system illustrated in FIG. 4, however, does not provide for substantial shadows in the viewed scene as might be desired. In such applications, it is then preferable to use the independent illumination sources 16 and 18 illustrated in FIG. 1.

FIG. 5 illustrates an alternative embodiment for the selector system 32 of the present invention. The selector system shown in FIG. 5 comprises a housing 80 which is rotated by the shaft 54 from the motor 52 and which in place of the prism reflectors and relay lens system illustrated in FIG. 1 contains an optical fiber bundle 82 which is placed to translate the image from the corresponding ends 34 or 36 of the fiber optic bundles 24 and 26 to the front surface 48 of the fiber optic bundle 38.

As can be understood from the above description of the preferred embodiment of the present invention and alternatives thereto, the present invention provides a simple and highly flexible system for direct optical viewing of a selected one of a plurality of remote scenes within a high pressure, typically fluid environment. In addition, the use of fiber optic bundles permit physical flexibility in positioning of one or more of the imaging systems to accommodate different scenes that might be required in deep sea exploration or maintenance work.

While described above specifically with reference to a viewing system for a high pressure environment, it is to be understood that the fiber optic viewing system may be used in other hostile environments to translate the image of a remote object from plural selectable scenes to an observer generally located outside of the environment. An example of such an environment is where high energy radiation interference would be present.

The above-described preferred embodiments are exemplary only and are not to be taken as limiting of the invention, the scope of which is defined in the following claims.

What is claimed is:

1. A system for viewing a selected scene out of a plurality of selectable scenes within a high pressure environment, said system comprising:
a plurality of fiber optic bundles exposed to said environment;
means for forming an image of each of said plurality of selectable scenes for transmission by a corresponding one of said plurality of fiber optic bundles;
means for selecting one of the images transmitted by each of said fiber optic bundles;
a pressure hull between said high pressure environment and a viewing region;
an optically transmissive window in said pressure hull;
means for transmitting the selected image from said plurality of fiber optic bundles through said window; and
means to permit viewing of the image transmitted through said window whereby the selected scenes may be optically monitored.

2. The system of claim 1 further including means for illuminating the plurality of scenes in said high pressure environment.

3. The system of claim 2 wherein said illuminating means further includes means for transmitting illumination radiation through said window for transmission along the path of the selected image to the selected scene for illumination thereof.

4. The system of claim 1 wherein said means for selecting a transmitted image from a corresponding one of said plurality of fiber optic bundles includes a rotatable periscopic structure having an image output to said means for transmission through said window, an image input, means for transmitting an image from said image input to said image output, and means for rotating said image input to receive the transmitted image from each of said plurality of fiber optic bundles.

5. The system of claim 4 wherein said means for transmitting an image between said image input and image output includes first and second reflectors and a relay lens system therebetween.

6. The system of claim 4 wherein said means for transmitting an image between said image input and said image output includes a fiber optic bundle exposed to said environment.

7. The system of claim 1 wherein said means for transmitting the selected image through said window includes a fiber optic bundle between said means for selecting a transmitted image and said window.

8. The system of claim 1 wherein said means for permitting viewing includes a first optical element adjacent said window and within said high pressure environment and a second optical element on the opposite side of said window through which the selected image may be viewed.

9. The system of claim 8 wherein said means for transmitting the selected image through said window includes a fiber optic bundle exposed to said environment and extending from said selecting means and terminating at said first optical element on the high pressure side of said window.

10. The system of claim 8 wherein said second optical element includes a field lens adjacent said window and an eyepiece for use by an observer.

11. A system for viewing a selected scene out of a plurality of selectable scenes within a hostile environment, said system comprising:
a plurality of fiber optic bundles exposed to said environment;
each of said fiber optic bundles having a first surface at one end thereof and a second surface at an opposite end thereof and functioning to translate an image plane from said first surface to said second surface;
means for forming an image of each of said plurality of selectable scenes on a first surface of a corresponding one of said plurality of fiber optic bundles whereby an image of each of said scenes is transferred to the second surface of a corresponding one of said plurality of fiber optic bundles;
an optical commutator system having:
a plurality of image receiving stations to which the second surface of each of said plurality of fiber optic bundles is applied;
an optical image exit station;
means for transferring an image from a selected one of said image receiving stations to said image exit station; and
means for positioning said image transferring means at a selected image receiving station; and
means for permitting operator viewing of the image at said image exit station of said rotatable optical commutator at a location remote from said plurality of scenes.

12. A system for viewing a selected scene out of a plurality of selectable scenes within a high radiation environment, said system comprising:
a plurality of fiber optic bundles exposed to said environment;
means for forming an image of each of said plurality of selectable scenes for transmission by a corresponding one of said plurality of fiber optic bundles;
means for selecting one of the images transmitted by each of said fiber optic bundles;
a partition between said high radiation environment and a viewing region;
an optically transmissive window in said partition;
means for transmitting the selected image from said plurality of fiber optic bundles through said window; and
means to permit viewing of the image transmitted through said window whereby the selected scenes may be optically monitored.

* * * * *